United States Patent [19]

Namura et al.

[11] 3,950,942

[45] Apr. 20, 1976

[54] CONTROL APPARATUS FOR A WARP KNITTING MACHINE

[75] Inventors: Yukio Namura, Fukui; Tooru Mashimo; Tadao Kosaka, both of Gukui; Kooichi Ofude, Komatu, all of Japan

[73] Assignee: Kabushiki Kaisha Matsuura Kikai Seisakusho, Japan

[22] Filed: Apr. 22, 1974

[21] Appl. No.: 463,111

[30] Foreign Application Priority Data

Apr. 26, 1973 Japan.............................. 48-480747

[52] U.S. Cl................................ 66/86 C; 66/154 A
[51] Int. Cl.²................... D04B 23/00; D04B 27/00; D04B 15/66
[58] Field of Search.............. 66/154 CA, 154 R, 86; 192/2, 142; 318/685, 9, 10, 11, 12, 13, 14; 310/80

[56] References Cited
UNITED STATES PATENTS

| | | | |
|---|---|---|---|
| 3,089,322 | 5/1963 | Bruce et al. | 66/86 C |
| 3,402,308 | 9/1968 | Henscske | 310/80 |
| 3,453,510 | 7/1969 | Kreuter et al. | 318/685 X |
| 3,457,482 | 7/1969 | Sawyer | 318/685 X |
| 3,575,653 | 4/1971 | Guewa | 318/685 |
| 3,626,725 | 12/1971 | Fertig et al. | 66/86 L |
| 3,628,119 | 12/1971 | Abraham | 318/685 |
| 3,630,052 | 12/1971 | Fertig et al. | 66/86 L |
| 3,660,704 | 5/1972 | Paine et al. | 310/80 |
| 3,668,904 | 6/1972 | Murenbeeld | 66/86 L |
| 3,762,184 | 10/1972 | Schur et al. | 66/86 R |
| 3,777,245 | 12/1973 | May | 318/685 |

Primary Examiner—Ronald Feldbaum
Attorney, Agent, or Firm—McGlew and Tuttle

[57] ABSTRACT

The guide bars of a warp knitting machine are automatically controlled in accordance with a desired pattern in synchronism with the rotation of a main shaft of the machine through control apparatus comprising a memory capable of storing information on a pattern of stitches to be formed, a control controlling rotation of the main shaft and giving instructions to the memory to produce a pattern signal for each course, a signal distributor receiving the pattern signals from the memory, and respective servo drive mechanisms for each guide bar and each including a servo motor. Responsive to the pattern signal from the signal distributor, each servo motor controls the length of linear movement of its associated guide bar. The signal distributor is a pulse distributor, and the pulses are effective to step the servo motors through predetermined angles of rotation with the rotation of each servo motor being converted into a corresponding linear displacement of an element for operating the associated guide bar.

17 Claims, 18 Drawing Figures

CONTROL APPARATUS FOR A WARP KNITTING MACHINE

SUMMARY OF THE INVENTION

This invention relates to a control apparatus for a warp knitting machine, particularly for a Rechel knitting machine.

Heretofore, it has been usual practice to use a pattern chain device for effecting control of the operation of a Rachel warp knitting machine so as to move the guide bars of the knitting machine as desired to produce knitted fabrics or knittings of the desired pattern. As is well known, the pattern chain device comprises a plurality of pattern chains equal in number to the guide bars and each comprising a number of links which differ from one another in shape and serving as cams having heights corresponding to the desired amounts of movements of the respective guide bars.

The use of the aforementioned pattern chain device as a means for controlling the operation of a warp knitting machine involves the use of chains each of which has a length corresponding to one cycle of operation of the guide bars for producing knittings of the desired pattern. This makes it necessary to use chains of a great length when the desired pattern is a complicated one, so that the space occupied by the chains is large and the control device is complex in construction. For example, the links of each chain serving as cams are complex in construction and it is troublesome to arrange them according to the movements of the guide bars required for producing knittings of the desired pattern. Such links of the chains must be rearranged each time one pattern is replaced by another pattern in producing knittings. This is time consuming and requires a lot of manual attention, thereby unfavorably affecting the productivity of the warp knitting machine.

In knitting fine net-like fabrics or laces, for example, ten to twenty guide bars are usually employed. A warp knitting machine is usually constructed such that about 38 guide bars can be provided therein. Each of these bars should be controlled individually in its movement. The aforementioned pattern chain device of the prior art heretofore used for controlling the movements of the guide bars according to the desired pattern of the knittings to be produced is constructed such that one pattern chain is provided for each guide bar as aforementioned. Thus, an increase in the number of guide bars makes the assembling of the chain links more troublesome and makes the pattern chain device more complex in construction. In addition, the use of the chains makes a considerable noise.

SUMMARY OF THE INVENTION

This invention has as its object the provision of a control apparatus for a warp knitting machine which obviates the aforementioned disadvantages of the prior art and which is simple on construction and reliable in performance.

Particularly, the invention aims at obviating the problem of how to control a warp knitting machine in such a manner that a mechanical output power obtained by conversion of an electric pattern signal is mechanically amplified so as to thereby control the amount of a movement of each guide bar of the warp knitting machine.

The aforementioned object of the invention is accomplished by providing a control apparatus which eliminates the need to use pattern chains and which employs servo drive mechanisms, e.g. step motors, hydraulic motors or the like, controlled by instructions given by a miniature electronic computer, the amount of a rotational movement of each motor being converted into the amount of a linear movement for controlling the amount of a movement of each guide bar through the agency of a push rod.

An outstanding characteristic of the present invention is that any pattern of the knittings to be produced is stored in a memory of the electronic computer of the control apparatus according to a stored program system, and instructions are given to the stepping motors according to an incremental system. More specifically, instructions on the pattern of the knittings to be produced are given to the servo drive mechanisms, e.g. stepping motors, in the form of the linear displacement of the guide bars by control means from the memory of the computer. The spacing between the adjacent needles or one pitch of the needles is generally set at a predetermined value of 1.4 millimeters, for example, and the number of pulses necessary for operating the stepping motors to move the guide bars a distance corresponding to one pitch of the needles is generally set beforehand at any value as desired or 12, for example. Thus, the direction and amount of a displacement of each guide bar from one position to the next following position are transmitted by the control means from the memory in the form of a pulse signal to the respective stepping motor.

The amount of a rotational movement of each pulse motor which is driven by a pulse signal from the memory of the computer is converted by means for converting a rotary movement into a linear movement, e.g. a pin drum arrangement or ball bearing screw assembly, into the amount of a linear displacement which is transmitted to the respective guide bar through the agency of a push rod and a push lever so as to move the guide bar a distance corresponding to the amount of linear displacement given by the instructions. Instructions on the distance to be covered by the linear displacement of each guide bar are given such that the distance is expressed in terms of an integral multiple of the pitch of the needles or the spacing between the adjacent needles.

The use of the control apparatus according to the invention eliminates the need to use a conventional pattern chain device. As a result, there is no trouble of rearranging the links of each chain each time knittings of a new pattern are to be produced. Any pattern as desired may be analyzed by a pattern analyzer and stored in the memory of the computer or stored in the memory of the computer by using a punched tape or other information recording medium in which necessary information on the desired pattern is manually recorded. This facilitates the changing of the patterns of the knittings to be produced by the warp loom in which is incorporated the control apparatus according to the invention. Additional advantages offered by the invention are that the noise produced by the chains can be eliminated and that the space occupied by the control apparatus can be minimized.

BRIEF DESCRIPTION OF THE DRAWINGS

Other and additional objects and features of the invention will become evident from the description set forth hereinafter when considered in conjunction with the accompanying drawings, in which.

BRIEF DESCRIPTION OF THE PREFERRED EMBODIMENT

Figure 1:
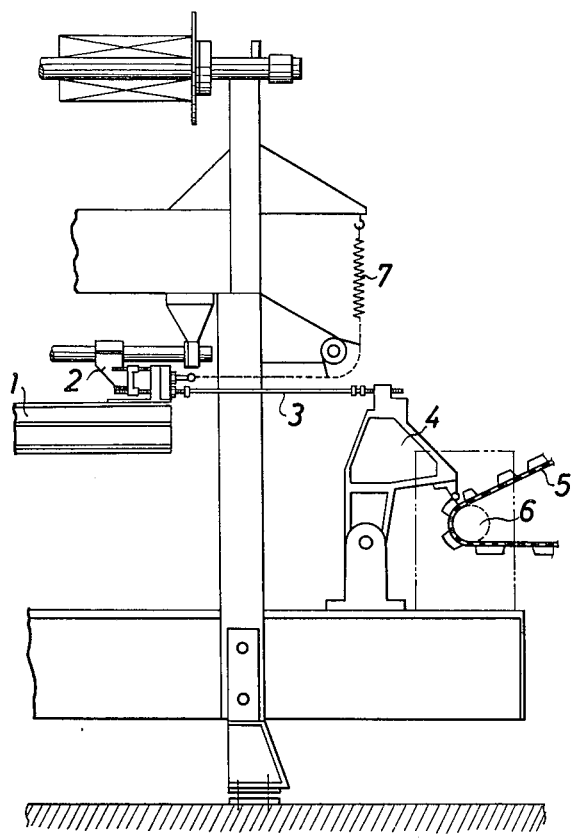
FIG. 1 is a fragmentary front view of a known warp knitting machine in which the control apparatus according to the invention can be incorporated.
Figure 2:
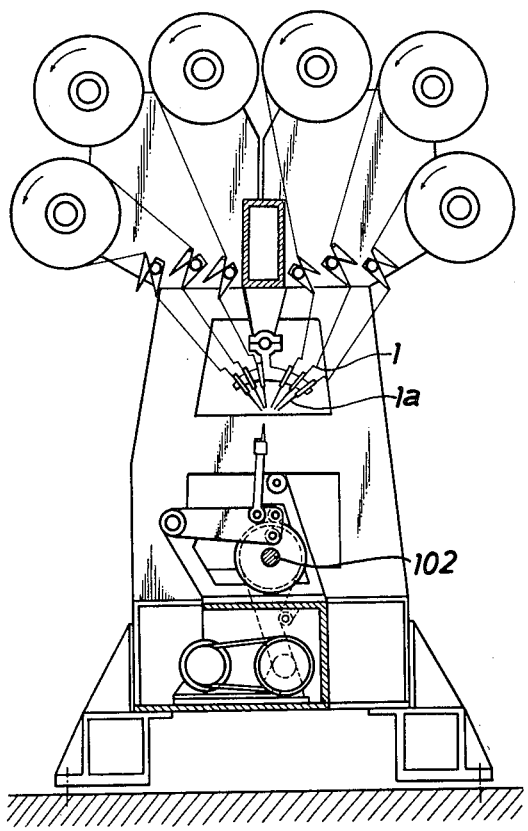
FIG. 2 is a side view of the warp knitting machine shown in FIG. 1.

Before describing the present invention, the pattern chain device heretofore used for controlling the operation of a wafp knitting machine will be outlined. The pattern chain device comprises, as shown in FIG. 1 and FIG. 2, a plurality of shogging levers 4 each for controlling, through a push lever 2 and a push rod 3, a guide bar 1 which supports guides 1a, a plurality of pattern chains 5 for controlling the respective shogging levers 4, drive means 6 for driving the respective pattern chains 5, and tension spring means 7 for pulling the push rods 3. The pattern chains each comprise a plurality of links which differ from one another in shape and serve as cams which each have a height corresponding to the distance covered by a movement of the respective guide bar 1. The shogging levers 4 function as cam followers for the links of the chains 5 functioning as cams. The movements of the shogging levers 4 are transmitted through the push rods 3 to the respective guide bars 1, so that the distance covered by a movement of each guide bar is controlled by changes in the height of the links of the chain.

Figure 3:
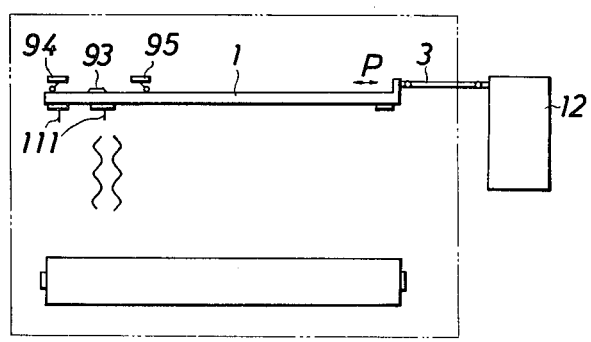
FIG. 3 is a schematic plan view showing the relation between one of the guide bars of the warp knitting machine and the control apparatus according to the invention.

In FIG. 3, there is shown a conventional warp knitting machine 11 of the type shown in FIG. 1 and FIG. 2 which incorporates therein a control apparatus 12 according to the invention.

Figure 6:
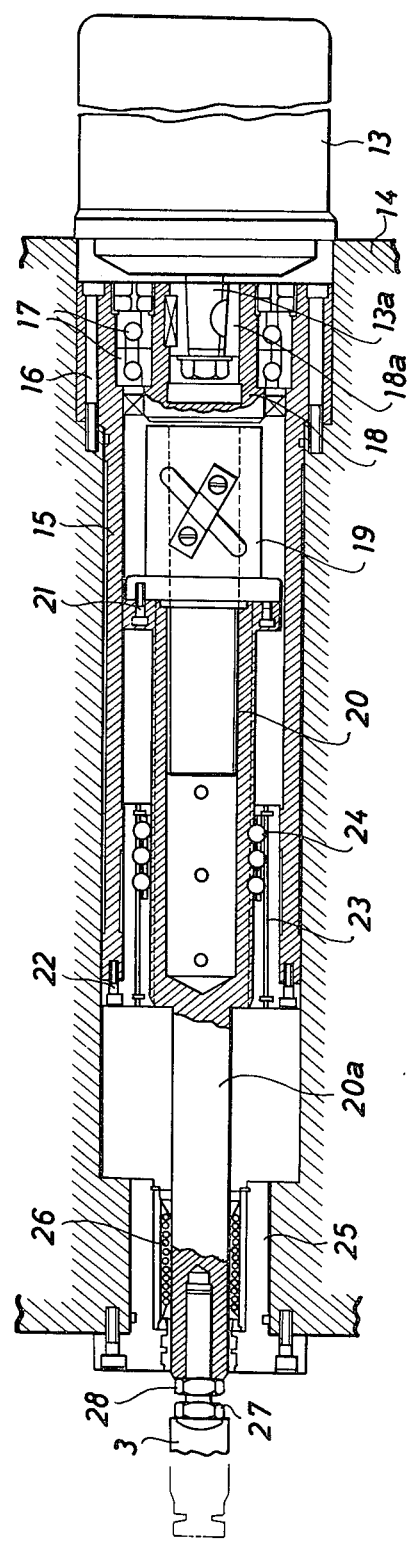
FIG. 6 is a sectional view of one embodiment of the stepping motor device comprising a stepping motor and a means for converting a rotary movement into a linear movement.

One embodiment of the control apparatus 12 according to the invention comprises a plurality of stepping motor devices each comprising a stepping motor and a means for converting a rotary movement into a linear movement directly connected to the stepping motor. FIG. 6 shows one of the stepping motor devices comprising a stepping motor 13 secured to a frame 14 to which is also secured, as by bolts 16, a cylindrical casing 15 for the means for converting a rotary movement into a linear movement.

A threaded shaft 18 is rotatably supported in the interior of the casing 15 at one end portion thereof through a ball bearing 17. The stepping motor 13 has an output shaft 13a over which is fitted a sleeve 18a inserted into one end portion of the threaded shaft 18 and keyed or otherwise secured thereto. The sleeve 18is keyed or otherwise secured to the output shaft 13a so that they may not rotate relative to each other. Threadably connected to the threaded shaft 18 is a nut 19 to which is coaxially secured a ball spline shaft 20 as by bolts 21. The ball spline shaft 20 is supported for axial sliding motion through balls 24 by a ball spline sleeve 23 affixed by screws 22 to the other end portion of the casing 15.

The ball spline shaft 20 is formed therein with an axially extending actuating bar 20a which is supported for axial sliding motion through a ball slide bearing 26 by a sleeve 25 secured to the frame 14. The actuating bar 20a has an adjusting bolt 27 threaded into its forward end for effecting fine adjustment, and which can be fixed in an adjusted position by a lock nut 28. Each push rod 3 is maintained in pressing engagement with the head of one of the adjusting bolts 27, or at the forward end of the actuating bar 20a.

When the output shaft 13a of the step motor 13 shown in FIG. 6 rotates through an angle corresponding to the number of pulses given as instructions by control means from the memory of the computer, the threaded shaft 18 rotates through the same angle as the output shaft 13a. This causes the nut 19 and hence the ball spline shaft 20 to move axially a distance corresponding to the angular displacement of the threaded shaft 18 either rightwardly or leftwardly in FIG. 6, the direction of axial movement of the spline ball shaft 20 varying depending on the direction of angular rotation of the threaded shaft 18. The axial movement of the ball spline shaft 20 either causes the push rod 3 to be pushed leftwardly or causes the same to move rightwardly in FIG. 6 for a distance as desired. In the embodiment shown and described, the stepping motor devices affixed to the frame 14 and each comprising a stepping motor and a means for converting a rotary movement into a linear movement are equal in number to the push rods 3. The threaded shaft 18 and nut 19 may be in the form of a ball screw arrangement.

The stepping motor devices shown in FIG. 6 may be replaced by another form of drive mechanism shown in FIG. 7 to FIG. 10. In the embodiment shown in FIG. 6, each stepping motor is directly connected to the respective push rod, so that the load of the push rod is directly applied to the output shaft 13a of the stepping motor 13. This makes it necessary to use stepping motors of a high output power which are inevitably large in size. In order to eliminate the need to use stepping motors of large capacity, the drive mechanism shown in FIG. 7 to FIG. 10 comprises a plurality of stepping motor devices each comprising a stepping motor A similar to the stepping motor 13 of FIG. 6 but producing a lower output power, and a power increasing means B for increasing the output power of the stepping motor A to a level such that is sufficiently high to push and move the respective push rod 3 and guide bar 1. The output power increasing means B shown in FIG. 7 to FIG. 10 is a pin and drum arrangement.

In the embodiment shown in FIG. 7 to FIG. 10, any other servo-mechanism than the stepping motor device shown in FIG. 6 may be used as a device for converting a pattern instructions signal into an output power for moving each guide bar. For example, such servomechanism may comprise means for detecting the amount of a linear movement (Magnescale produced by Sony Company, for example) which is used to detect the amount of a linear movement of each guide bar, and the detected values are used by feedback to control the operation of hydraulic motors through electro-hydraulic servo valves.

Figure 7:
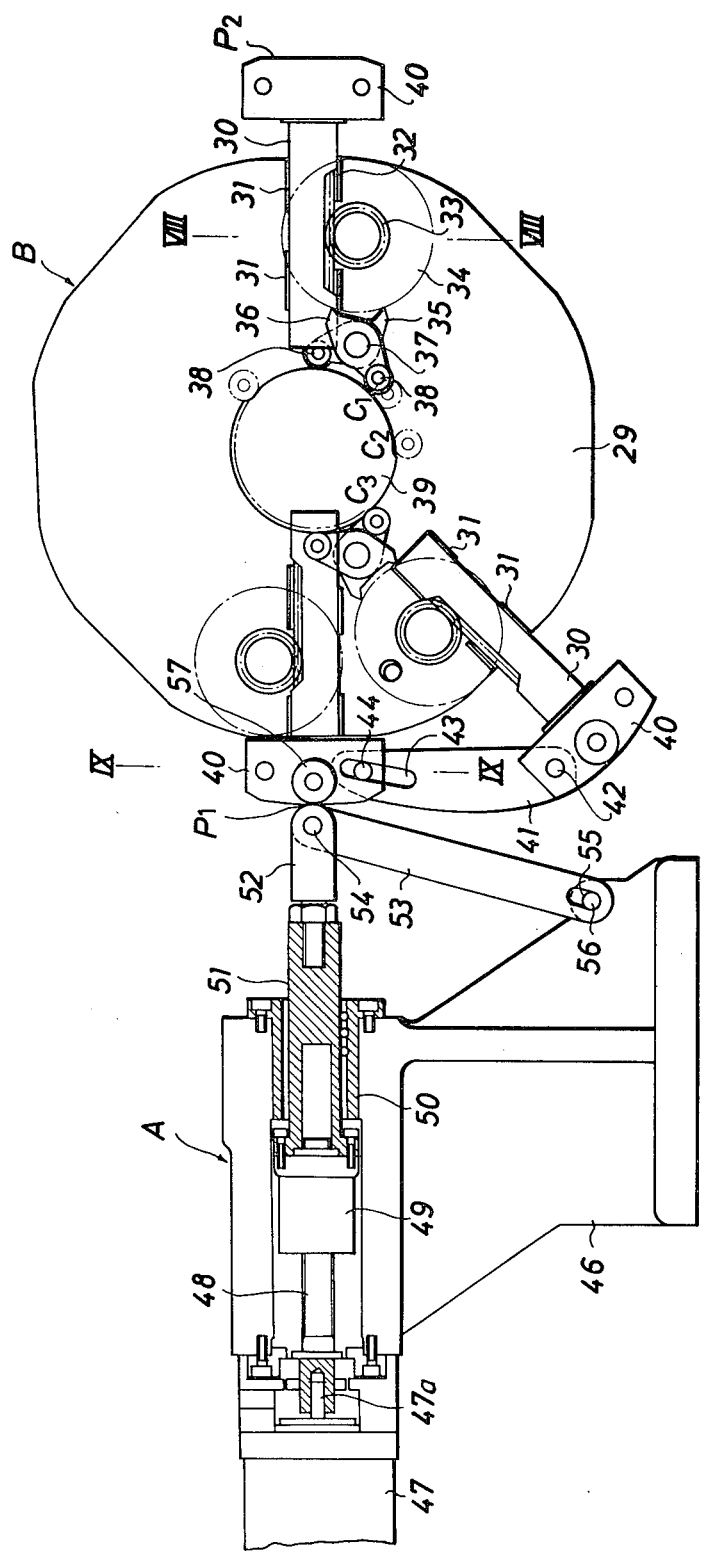
FIG. 7 is a front view of the stepping motor device and the pin drum arrangement.

In FIG. 7, a drum 29 is rotatably mounted on the frame 14 and has a plurality of pins 30 (eight pins are provided in FIG. 7) arranged radially on the drum 29 and each slidably supported by a bearing 31. Each pin 30 is formed in one portion of its outer periphery with a rack 32 with which a pinion 33 is maintained in meshing engagement.

Figure 8:
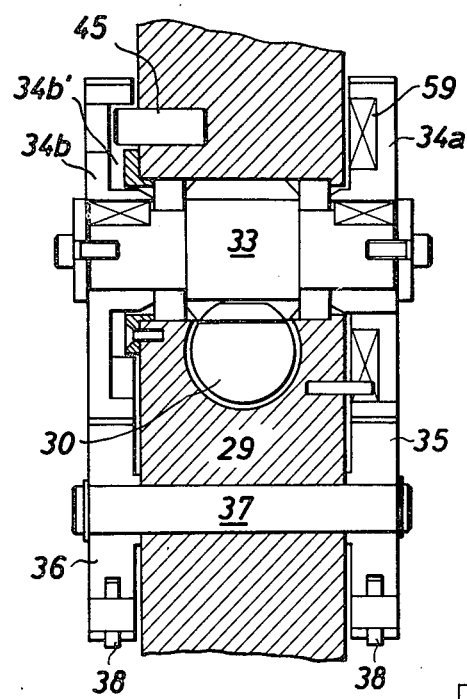
FIG. 8 is a sectional view taken along the line VIII—VIII of FIG. 7.
Figure 9:
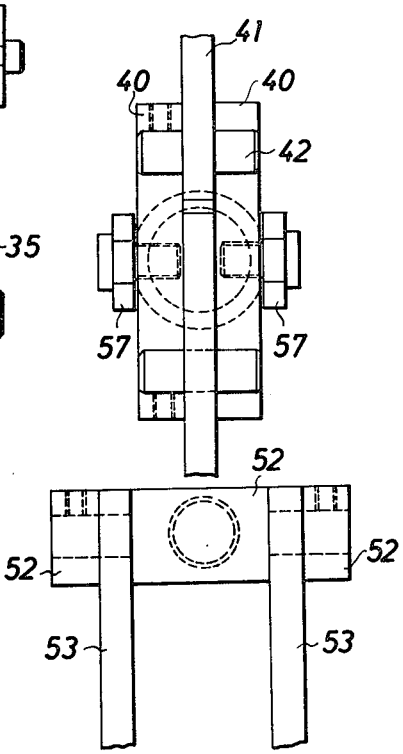
FIG. 9 is a sectional view taken along the line IX—IX of FIG. 7.

Each pinion 33 is rotatably supported on the drum 29 and formed integrally with a ratchet wheel 34. A first pawl 35 is brought into engagement with each ratchet wheel 34 to prevent its clockwise rotation, and a second pawl 36 is brought into engagement with each ratchet wheel 34 to prevent its counter clockwise rotation, the first and second pawls 35 and 36 being pivotally supported by a pin 37 affixed to the drum 29. As shown in FIG. 8, each ratchet wheel 34 preferably comprises a ratchet wheel member 34a with which the first pawl 35 is brought into engagement and a ratchet wheel member 34b with which the second pawl 36 is brought into engagement. The first pawl 35 and second pawl 36 rotatably support at the rear end thereof rollers 38 which move in rolling motion along the outer periphery of a fixed cam 39 disposed coaxially with the drum 29. The cam 39 comprises a cam member for the first pawls 35 and a cam member for the second pawls 36. The pawls 35 and 36 are under the influence of springs (not shown) so as to bring the rollers 38 into pressing engagement with the cam 39.

Each pin 30 has affixed to its free end a cam plate 40 for transmitting the movement of the pin 30 to the respective shogging lever. No matter how closely the adjacent pins 30 and consequently the adjacent cam plates 40 are disposed with each other, there will be produced differences between the cam plates 40 in their positions, because the pins 30 move radially of the drum 29 according to the desired pattern of the knittings to be produced and the distances covered by the adjacent pins vary from each other in most cases. The cam plates 40 disposed in different positions move the shogging lever for different distances while rotating with the drum 29. As a result, the shogging lever may move into a space between the adjacent pins and strike against the next following pin 30. In order to facilitate the transmission of changes in the position of the cam plates 40 to the shogging lever, a bridge 41 is mounted between the cam plates 40 of the adjacent pins 30. Each bridge 41 is pivotally connected at one end thereof by a pin 42 to one cam plate 40, and formed at the other end thereof with a slot 43 in which is engaged a pin 44 affixed to the adjacent cam plate 40. By this arrangement, the shogging lever can be smoothly brought into engagement with one cam plate 40 after another by sliding along the bridges 41.

Each stepping motor device A is positioned against one of the drums 29 in any manner as desired, and comprises a stepping motor 47 including an output shaft 47a, and a means for converting a rotary movement into a linear movement comprising a threaded shaft 48 affixed to the output shaft 47a, a nut 49 threadably fitted over the threaded shaft 48, and a ball spline shaft 51 coaxially affixed to the nut 49 and engaged in a ball spline sleeve 58 affixed to a bracket 46. The ball spline shaft 51 has threaded into its free end a forked contact member 52 whose position can be adjusted freely. A guide link 53 is pivotally connected at one end thereof by a pin 54 to the forked contact member 52, and formed at the other end thereof with a slot 55 which receives therein a pin 56 affixed to the bracket 46.

Upon rotation of each stepping motor 47 as a pulse signal is supplied thereto from the memory of the computer by instructions given by the control means, the nut 49 and ball spline shaft 51 move either leftwardly or rightwardly in FIG. 7 for a distance as desired which corresponds to the angle through which the stepping motor 47 rotates, the direction of movement of the nut 49 and ball spline shaft 51 varying depending on the direction of rotation of the stepping motor 47. This causes the contact member 52 to move for a desired distance in a desired direction. That is, the movement of the forked contact member 52 brings each pin 30 of the pin drum arrangement B associated with the stepping motor device A to its operative position. To be more specific, when one of the pins 30 is brought into contact with the forked contact member 52 which has moved for a desired distance, the pin 30 is moved for a desired distance toward the center of the drum 29 which is rotating at all times, so that the forked contact member 52 is brought into siding contact with the pin 30. To eliminate the possibility of production of frictional dragging of the contact member 52 on the cam plate 40 of the pin 30, a roller 57 is mounted at each side of the cam plate 40, so that the end portion of the forked contact member 52 is brought into rolling contact with the rollers 57.

Each pin 30 of the pin drum arrangement B is brought to an operative position which corresponds to one course of several courses for the desired pattern according to the instructions given on the stiches to be formed. Then, each pin transmitts the instructions given to it to the respective push rod so as to vary the position of the respective guide bar according to the desired pattern.

As aforementioned, eight pins 30 are provided on the drum 29 in FIG. 7. In this type of pin drum arrangements B, instructions are given from the stepping motor devices A to the guide bars on eight course of stitches while the drums 29 make one complete revolution.

While each drum 29 rotates, each pin 30 on the drum 29 is moved radially of the drum 29 for a desired distance by the associated stepping motor device A or other output device when it is disposed in a predetermined position $P_1$. Thus, each pin 30 is moved into an operative position according to the desired pattern and gives instructions to the respective push rod, directly or through the respective shogging lever, on a change in the pattern when the pin 30 is brought to a second predetermined position $P_2$ after the drum 29 has made one half revolution. That is, the pin 30 disposed in this position $P_2$ moves the respective guide bar linearly for a desired distance, thereby transmitting the instructions on a change in the pattern. The pins 30 of all the pin drum arrangements B simultaneously transmitt instructions to all the guide bars, so that instructions on a change in the pattern can be transmitted to all the guides.

Figure 10:
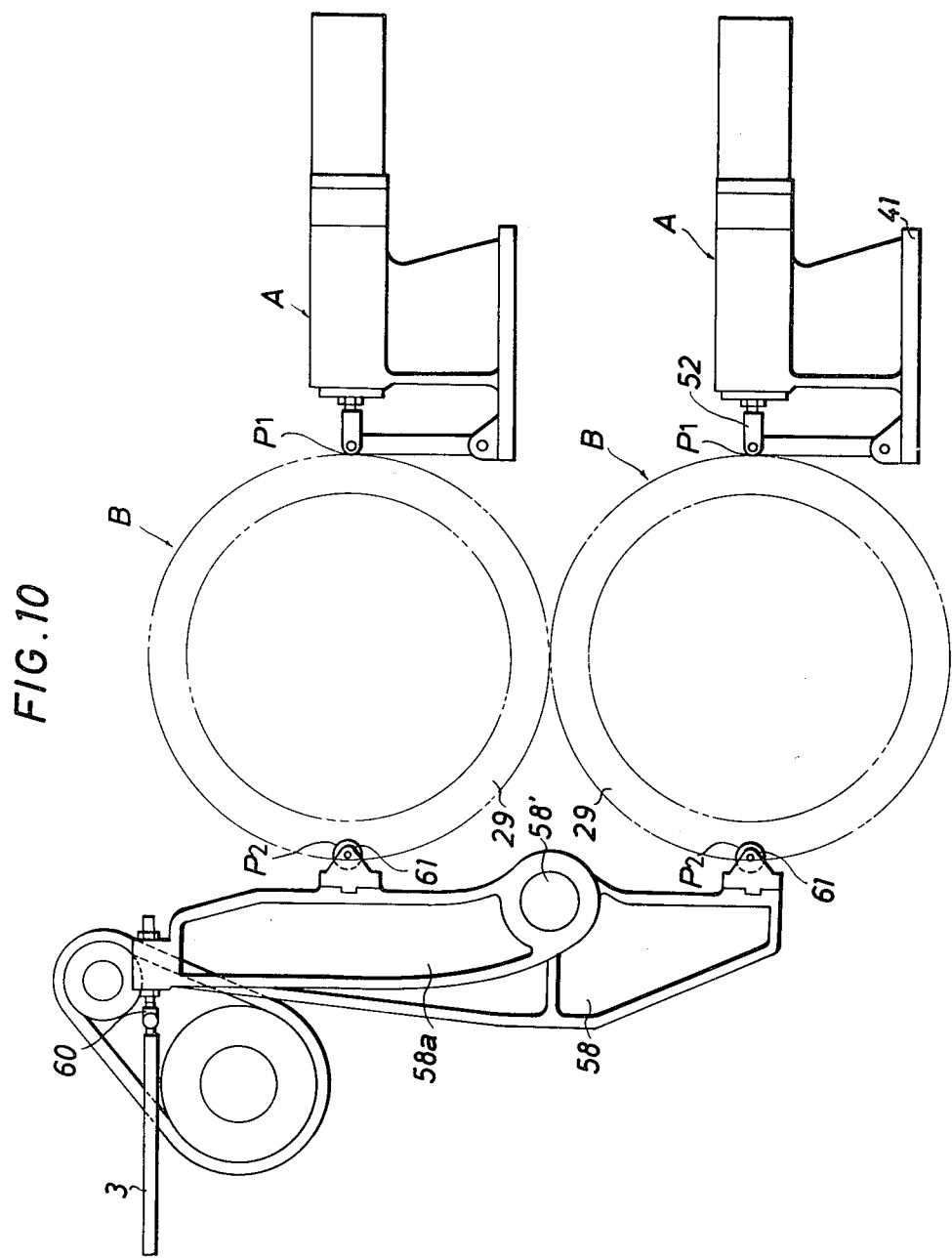
FIG. 10 shows the arrangement of the stepping motor devices and pin drum arrangements in relation to the push rods.

After each pin 30 and its cam plate 40 have transmitted instructions to the associated shogging lever 58 to move the associated guide bar for a desired distance at the position $P_2$ shown in FIG. 7 and FIG. 10, the roller 38 on the pawl 35 is brought into engagement with a major diameter portion of the cam 39 at a point $C_1$, as the drum 29 rotates. When the roller 38 comes to this position $C_1$, the pawl 35 moves in pivotal movement about the pin 37 into a position shown in FIG. 8, and the ratchet wheel 34a is caused to rotate by the biasing force of a spiral spring 59 connected at one end to the drum 29 and at the other end to the ratchet wheel 34a. This causes the pinion 33 to rotate to move the pin 30 radially outwardly of the drum 29 into its outermost position which is limited by the length of the rack 32 or by a pin 45 affixed to the drum 29 cooperating with an arcuate groove 34b' formed on the surface of the ratched wheel 34. Dislodging of each pin 30 is prevented by the pin 33 being in meshing engagement with rack 32 or by the engagement of the pin 45 with the arcuate groove 34b'. When the rotation of the drum 29 brings the roller 38 of each pawl 36 into engagement with a major diameter portion of the cam 39 at a point $C_2$, the associated ratchet wheel 34 is released.

As rotation of the drum 29 brings each pin 30 and its cam plate 40 near to the position $P_1$ in which the pin 30 will be positioned against the forked contact member 52 of the associated stepping motor device A, the rollers 57 on the cam plate 40 are brought into contact with the guide 53, so that the pin 30 is gradually moved radially inwardly of the drum toward the center of the latter. Upon moving to the position $P_1$, the cam plate 40 is brought into engagement with the forked contact member 52, thereby bringing the pin 30 to its operative position. Slightly before the pin 30 reaches the position $P_1$, or when the roller 38 of the pawl 35 is brought into engagement with a minor diameter portion of the cam 39 at a point $C_3$, the pawl 35 moves in pivotal movement about the pin 37 into engagement with the associated ratchet wheel 34a, thereby keeping the pin 30 from moving radially outwardly of the drum from its operative position. As the drum 29 rotates, the pin 30 which is brought to its operative position by the forked contact member 52 and moves to the next position $P_2$ while being maintained in such operative position, where it actuates the associated shogging lever 58 according to the instructions given to the pin 30. Before the pin 30 is brought to the second position $P_2$ by the rotation of the drum 29 to actuate the associated shogging lever 58, the roller 38 of the pawl 36 is brought into engagement with the minor diameter portion of the cam 39 at the point $C_3$, so that the pawl 36 is brought into engagement with the ratchet wheel 34b.

Each shogging lever 58 acted upon by the cam plate 40 of each pin 30 at the second position $P_2$ is pivotally supported by a shaft 58' and has connected to the other end thereof a receiver 60 which receives therein an end portion of the associated push rod 3. The receiver 60 is mounted such that its position can be adjusted as desired.

The shogging levers 58 are equal in number to the push rods 3, and the drive mechanisms each comprising the stepping motor device A and the pin drum arrangement B are also equal in number to the push rods 3. In order not to occupy more space than is necessary, the pin drum arrangements B and the stepping motor devices A are arranged both transversely and vertically as shown in FIG. 10. Thus, second shogging levers 58a each having a roller 61 mounted in a position other than the position in which the roller 61 is mounted in each shogging lever 58 for engagement with the cam plate 40 of each pin 30 may be used along with the shogging levers 58. The shogging levers 58 and 58a are supported by the same shaft 58'.

Referring to FIG. 7, the forked contact member 52 is not moved instantaneously from one position to another while the drum 29 rotates, but a certain time lapses before it moves to the next position. Thus, the forked contact member 52 moves relative to the rollers 57 of the pin 30. The positions of the adjacent pins 30 radially of the drum 29 may differ either slightly of greatly. If, for example, instructions are given to move the first pin 30 only for a short distance radially of the drum 29 toward its center and to move the next following pin 30 for a great distance, the next following pin 30 will strike against the forked contact member 52 of the stepping motor device A.

In order to preclude damage to the parts by this collision, the guides 53 are provided so that the rollers 57 on the pin 30 are first brought into engagement with the guide 53 and roll along the guide 53 before the forked contact member 52 is brought into engagement with the cam plate 40 of the pin 30 at the first position $P_1$. By this arrangement, one pin 30 after another can be brought into engagement with the forked contact member 52 without any trouble.

In some cases, the guide members 53 cannot perform the function of causing the forked contact member 52 to be brought into engagement with one pin 30 after another smoothly. For example, when instructions are given to move one of the pins 30 for a greatest possible distance radially of the drum 29 toward its center and not to move the next following pin 30, the forked contact member 52 moves gradually rearwardly as the associated stepping motor operates after pushing and moving the first pin 30 to the maximum. Since the drum 29 rotates, the bridge 41 between the first and the next following pins 30 may be brought into engagement with the guide before the next following pin 30 moves to the first position $P_1$, and the bridge 41 may thus be pushed by the guide 53, so that the next following pin 30 may be pushed and moved radially of the drum without complying with the instructions.

On the other hand, the pin 30 is kept from moving radially outwardly of the drum 29 before it reaches the second position $P_2$ once it has been pushed and moved radially inwardly thereof. Thus, when the next following pin 30 reaches the second position $P_2$, it has been moved more or less. That is, when the next following pin 30 receives instructions on its position from the stepping motor device in the first position $P_1$, the cam plate 40 of the next following pin 30 will be in a position in which it is not brought into engagement with the forked contact member 52, so that the pin 30 moving to the second position $P_2$ will carry incorrect information.

In order to obviate this defect, the relative positions of the guide 53 and each of the associated bridges 41 are such that they are never brought into engagement with each other. As a result, the forked contact member 52 transmits instructions to each pin 30 by being brought into the rollers 57 without directly coming into engagement with the cam plate 40.

In each pin drum arrangement, the teeth of the ratchet wheels 34a and 34b are spaced apart from one another a distance which is sufficiently great to move the associated guide bar a distance corresponding to one pitch of the needles. By this arrangement, it is possible to move the guide bars 1 a distance corresponding to the predetermined number of pitches even if there are errors in the number of pulses when the stepping motor is driven, thereby avoiding the danger of the guide striking against the needle as the result of the guide bar moving for a distance which is not in accord with predetermined one.

Figure 11:
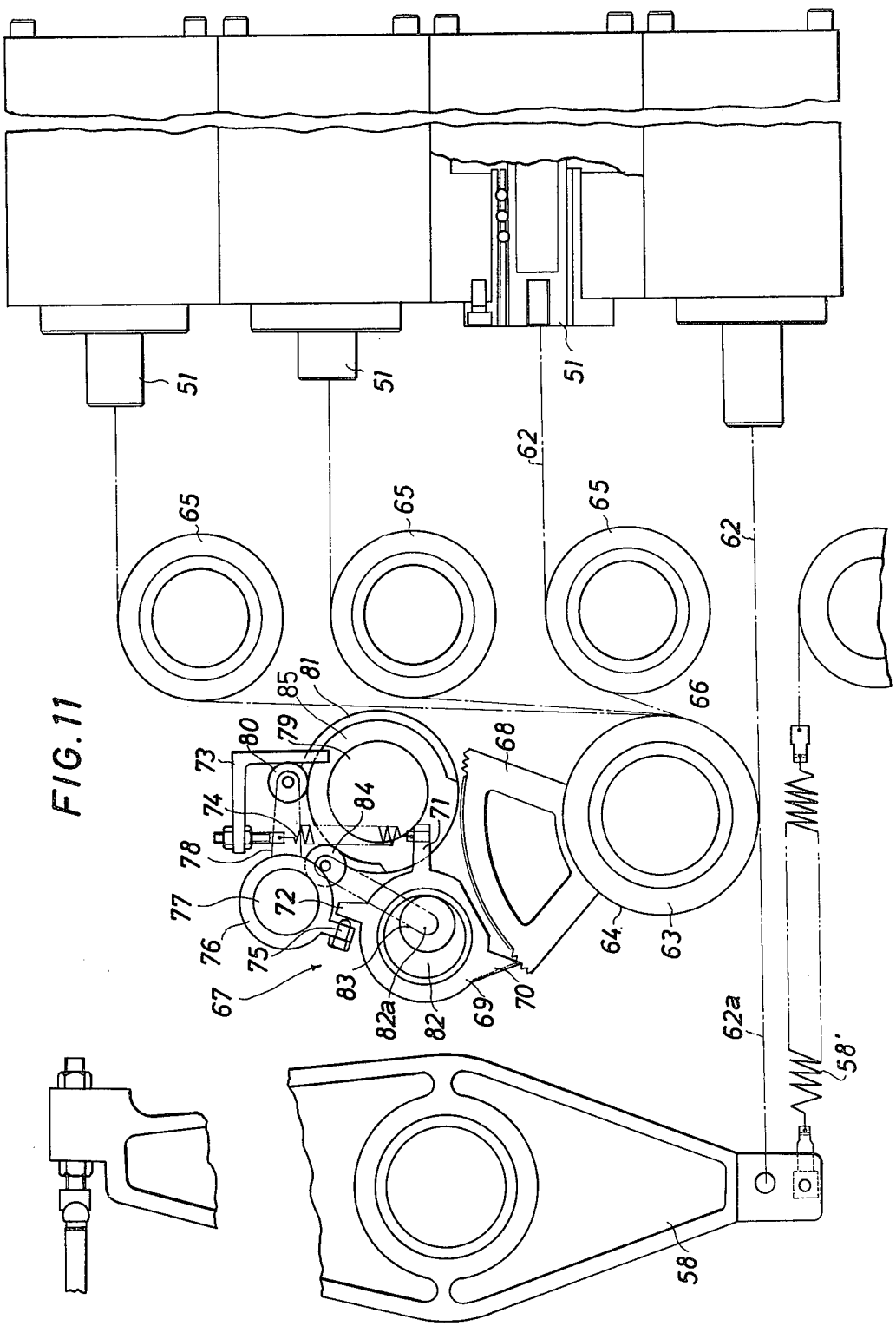
FIG. 11 shows stepping motor devices comprising another embodiment of the invention connected to a safety device.

FIG. 11 shows a third embodiment of the drive mechanism for the control apparatus according to the invention in which a wire, steel band, chain or other tension transmitting flexible member 62 (hereinafter referred to as a wire) is connected at one end to the forward end of the ball spline shaft 51 of the means for converting a rotary movement into a linear movement of each stepping motor device shown in FIG. 7 and at the other end to a point 64 on the outer peripheral surface of a drum 63. Each wire 62 is guided by a suitable guide drum 65 disposed in suitable position.

The linear movements of each ball spline shaft 51 produced by instructions in the form of pulses given by the control means from the memory are transmitted through the associated wire 62 to the drum 63 which is rotated through an angle corresponding to the distance covered by a linear movement of each ball spline shaft 51 each time the instructions are transmitted. Each drum 63 is connected to the associated shogging lever 58 through a wire 62a. More specifically, the wire 62a is connected at one end to a point 66 on the outer peripheral surface of the associated drum 63 and at the other end to one end portion of the associated shogging lever 58. The rotary movement of the associated drum 63 is transmitted through each wire 62a to the associated shogging lever 58 which moves linearly a distance corresponding to the amount of rotary movement of the drum 63. The movement of each shogging lever 58 is transmitted through each push rod 3 to the associated guide bar 1.

Each shogging lever 58 is under the influence of the biasing force of a spring 58' which is sufficiently large to maintain the shogging lever 58 in a predetermined position against the biasing force of the associated push rod 3 even when the shogging lever 58 is not subjected to the tensile force exerted by the wire 62'. The drive mechanism comprises a correction device generally designated 67 for transmitting the movements of the ball spline shafts correctly to the shogging levers without being influenced by the loosening of the wires and errors in the number of pulses. Each correction means or device comprises a segmental ratchet wheel 68 mounted on the associated drum 63 and engaged by a pawl 70 of a ring 69 from which the pawl 70 projects outwardly. The ring 69 is also formed with a first arm 71 and a second arm 72 which project outwardly therefrom.

The first arm 71 is urged to move toward a bracket 73 affixed to a frame (not shown) by the biasing force of a spring 74, and thus maintained in engagement with an actuating projection 75 which is mounted on a ring 76 keyed or otherwise affixed to a shaft 77.

An arm 78 is affixed at one end to one end of shaft 77 and has mounted at the other end thereof a roller 80 which is maintained in pressing engagement with the outer peripheral surface of a cam 81. When the roller 80 is brought into engagement with a major diameter portion of the cam 81, the shaft 77 and ring 76 rotate and cause the projection 75 to push and move the second arm 72. Thus the ring 69 rotates clockwise in FIG. 11 about an eccentric shaft 82 on which it is mounted, thereby releasing the pawl 70 from engagement with the ratchet wheel 68. On the other hand, when the roller 80 is brought into engagement with a minor diameter portion of cam 81, the ring 69 is rotated by the biasing force of the spring 74 so as to thereby bring the pawl 70 into engagement with the ratchet wheel 68.

The eccentric shaft 82 has pivotally mounted about an eccentric axis 82a an arm 83 supporting at its end a roller 84 which is maintained in pressing engagement with the outer peripheral surface of a cam 85 mounted on a shaft 79. When the roller 84 is brought into engagement with a major diameter portion of the cam 85, the eccentric shaft 82 rotates about the eccentric axis 82a and the pawl 70 moves the ratchet wheel 68 counter clockwise for any distance as desired. The movement of the pawl 70 takes place in order to prevent the collision of a needle with the associated guide due to deviation of the associated guide bar from its correct position caused by an error in the number of pulses transmitted when the position of the associated shogging level 85 is adjusted by the associated stepping motor device. The pitch of the teeth of the ratchet wheel 68 is set beforehand such that the associated guide bar moves to a correct position when one of the teeth of the ratchet wheel 68 is brought to a next following engaging position after the pawl 70 has moved to a predetermined position.

Preferably, the drums 65 are in the form of tension drums so that the wires 62 may be tensioned at all times without being loosened by the action of the ratchet wheels 68.

Three embodiments of the control apparatus for moving the guide bars 1 according to the desired pattern of knittings to be produced may be controlled as described hereinafter.

Figure 12:
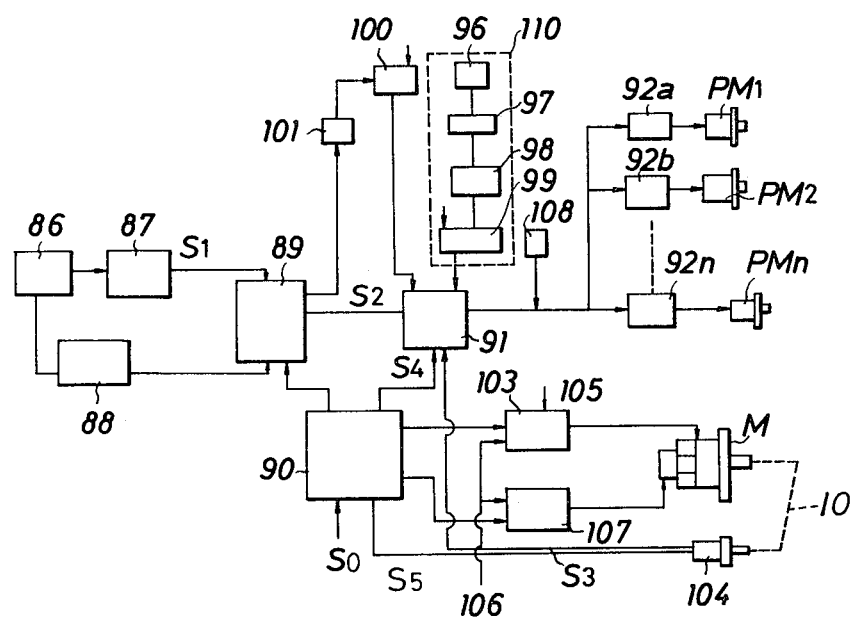
FIG. 12 is a block diagram of the control apparatus according to the invention.

As shown in FIG. 12 the control apparatus according to the invention further comprises a memory 89, e.g. an electronic computer. A pattern 68 of knittings to be produced may be analyzed by the pattern analyzer 87 and the information obtained by the analyzer may be directly or through a punched information card fed to the memory 89 in the form of electric signals $S_1$ and stored therein. Alternatively, the pattern 86 may be recorded in a punched tape or the information recording medium 88 manually and the information recorded therein may be stored in the memory 89. Thus, the storing of the necessary information is effected according to the stored program system in the present invention.

In the operation, at first a first course to be withdrawn from the memory 89 is instructed on a control means. Namely the instruction of the first course is fed to the memory 89 through the control means 90. The control means 90 then gives a signal, for driving a main motor M, to a main shaft speed control means 103 by instruction So given by push button. Simultaneously the control means 90 gives a signal, for withdrawing a pattern signal $S_2$, to the memory 89. The pattern signal $S_2$ for one course, withdrawn from the memory 89 is fed to a pulse distributor 91 and stored for a time in a buffer register disposed in the pulse distributor 91.

The rotation of a main shaft 10 driven with the main motor M is detected by a rotation angle detector 104. In each rotation of the main shaft a plurality of pulse trains $S_3$ are produced in a predetermined angle range of the main shaft and they are fed to the pulse distributor 91. One of the pulse trains $S_3$ is selected according to the pattern signal $S_2$ stored in the pulse distributor 91 and fed to a drive mechanism 92. To each drive mechanisms 92a, 92b -- 92n, which comprise stepping motor devices $PM_1$, $PM_2$ -- PMn respectively, a respective pulse train selected from the pulse trains $S_3$ according to the pattern signal $S_2$ is fed from the pulse distributor 91. The stepping motors of the stepping motor devices $PM_1$, $PM_2$ -- PMn each rotate through an angle corresponding to the number of pulses fed thereto through the pulse distributor 91. The guide bars 1 are moved linearly by the stepping motor devices PM through the push rod corresponding to the rotation angle of the associated stepping motor device. After knitting of the pattern according to, the one course signal $S_2$ the control means 90 gives a signal, for withdrawing a pattern signal $S_2$ of a following course, to the memory 89 by the signal $S_5$ given from the detector 104 detecting the completion of one course. Thereafter the operation cycle may be repeated.

The detector 104 producing a plurality of pulse trains $S_3$ comprises encoders connected to the main shaft and rotated with the main shaft and pulse generator S. Assuming that the length of maximum displacement of the guides is 14 pitches for example, seven encoders may be connected to the main shaft, and seven pulse trains can be obtained from the encoders. The pulse generator is constructed for producing 14 pulse trains according to the 7 pulse trains given from the encoders. Assuming that the number of pulses required for moving each guide bar 1 for a distance corresponding to one pitch of the needles, 12 signal pulses should be supplied to each stepping motor, so that $14 \times 12 = 168$ pulses are required for the maximum displacement 14 pitches. The pulse generator produces 14 pulse trains, each comprising a group of pulse trains produced by the encoder comprising seven trains each having 168, 156, 144, 132, 120, 108 and 96 pulses and another group of pulse trains comprising seven trains, the number of pulses of which is a divisor of the seven trains; 12, 24, 36, 48, 60, 72 and 84 pulses. In this case 14 encoders can be used, but a large space is required and it is expensive.

As aforementioned, the drive mechanisms 92 each comprising the stepping motor device PM are equal in number to the guide bars 1 of the warp knitting machine to be controlled. when the guide bar 1 is to be moved for a distance corresponding to two pitches of the needles, 24 pulses are supplied to each stepping motor.

Pulses are supplied for each course of stitches from the memory 89 to the pulse distributor 91. In other words, the pulses for one course constitute information necessary for controlling the movements of all the guide bars one time. This corresponds to the control of movements of the guide bars by the movements of one link of each pattern chain of the pattern chain device of the prior art.

The signal pulses for one course supplied from the memory 89 are divided into groups of pulses according to the distances to be covered by the movements of all the guide bars and distributed to the respective drive mechanisms 92.

Generally, the memory 89 has a capacity such that information on 300 to 800 courses of stitches can be stored therein.

Upon receipt of signal pulses from the pulse distributor 91, each stepping motor device PM is driven for one course after another, and the amount of the rotary movement of the output shaft of each stepping motor is converted into the amount of the linear movement of each ball spline shaft as aforementioned. The movement of each ball spline shaft moves the associated shogging lever either directly or indirectly so as to control the position of the associated guide bar through the associated push rod. After information on a predetermined number of courses of the desired pattern has been supplied from the memory 89 to the drive mechanisms 92, one cycle of operation is completed. The same instructions in the form of pulses are supplied from the memory to the drive mechanisms to repeat the same cycle of operation, so that a knitting wrought with a design consisting of a plurality of identical patterns can be produced.

In producing a knitting, the movements of the guide bars should be synchronous with the movement of a main shaft of the warp knitting machine which controls feeding of the thread and the movements of the needles. More specifically, when operation instructions $S_0$ are given to the control means 90, pattern instructions $S_2$ should be given from the memory 89 in synchronism with the rotation of the main shaft so as to thereby drive the guide bars. For that purpose the control means 90 gives a control instruction to the memory 89 and to the pulse distributor 91 replying to the signal from the rotation detector 104 detecting the rotation of the main shaft.

Generally, stitches of one course are formed while the main shaft 102 makes one complete revolution or rotates through 360°. Generally, stitches are formed by the needles during the time the main shaft makes an initial one-sixth revolution or rotates through 60° and during the time it makes a final one-sixth revolution or rotates through 60°, and the positioning of the guides is effected during the time the main shaft makes a two-third revolution or rotates through 240° between the initial and final 60°. To this end, instructions in the form of pulses given by the revolution angle detector 104 are given through the control means 90 to the pulse distributor 91. The pulses of a predetermined number are supplied to the pulse distributor 91 during the time the main shaft rotates through 240° in the intermediate period. The pulse distributor 91 is actuated upon receipt of these pulses.

Let us assume that the maximum number of pattern pulses for one course of stitches of the pattern is 168 which covers a distance corresponding to 14 pitches of the needles ($12 \times 14 = 168$).

Let us also assume that the number of pulses supplied to the pulse distributor 91 by instructions given by the rotation angle detector 104 while the main shaft 102 rotates through 240° is 168 and that the guide bars move a distance corresponding to one pitch of the needles when pattern instructions are given. Then, twelve pulses required for moving each guide bar are equally distributed among the 168 pulses from the control means 90. That is, one signal pulse is supplied to each drive mechanism each time fourteen pulses are supplied form the control means 90. When it is desired to move the guide bar a distance corresponding to fourteen pitches, one pattern signal pulse is produced each time one pulse is produced by the control means 90.

When each pin drum arrangement is constructed such that it is mechanically connected to the main shaft of the knitting machine and driven by the same drive source that drives the main shaft, the angle of rotation of each drum may be detected in place of detecting the angle of rotation of the main shaft.

When eight pins are provided for each drum and arranged redially on the drum, the angle formed by the adjacent two pins is 45°. Stitches are formed in the initial one-sixth and the final one-sixth of the angle 45° and the pattern signals are supplied to each drive mechanism from the pulse distributor in the intermediate two-thirds of the angle 45°.

The pin 30 disposed in the first position $P_1$ in FIG. 7 is disposed at the last stage of the intermediate two-thirds of 45°. During the time the drum rotates through the final one-sixth of 45° from the position shown in FIG. 7, the stepping motor device A remains inoperative and stitches are formed by the needles. Stitches are also formed by the needles during the time the drum 29 rotate through the initial one-sixth of the next 45°, and then the stepping motor device A is stopped operative during the time the drum 29 rotates through the intermediate two-thirds of the 45° when the ends of the forked contact member 52 are brought into engagement with the rollers 57 on the cam plate 40 of the next following pin 30, so that the pin 30 is brought to its operative position by the ball spline shaft 51 according to the pattern instructions.

The main shaft of the warp knitting machine can be driven in synchronism with the operation of the control apparatus according to the invention as aforementioned. An encoder of the rotary type connected to the main shaft either directly or indirectly may be used as the rotation detector 104 and made to rotate as the main shaft rotates. Such encoder 104 may generate a series of irregularly spaced pulses $S_3$, the spacing between two adjacent pulses increasing and decreasing according to the control pattern shown in FIG. 13. The pattern of spacing between the adjacent pulses of the series of pulses $S_3$ may be set beforehand so as to suit the performance of the step motor.

Figure 13:
FIG. 13 shows the pulse wave forms produced by the encoder.
Figure 15:
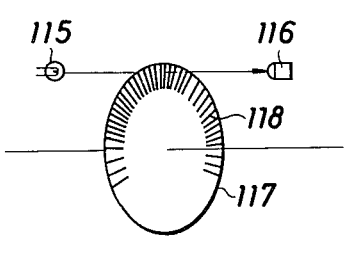
FIG. 15 shows the principle of the encoder on which a series of pulses is produced according to the pattern shown in FIG. 14.

FIG. 15 shows an example of the encoder in explanation of the principle with which the series of aforementioned irregularly spaced pulses are produced. The encoder 104 shown comprises a light intercepting rotary disc 117 interposed between a light source 115 and a light receiving element 116. The disc 117 is formed in its peripheral marginal portion with a multitude of light transmitting windows or slits 118, so that the light passing through such slits 118 can form the series of irregularly spaced pulses as shown in FIG. 13.

The aforementioned series of irregularly spaced pulses $S_3$ are supplied to the control means 90 shown in FIG. 12 which produces a signal $S_4$ according to the series of irregularly spaced pulses $S_3$ to control the pulse distributor 91. Thus, the step motors $PM_1$, $PM_2$-- $PMn$ are controlled such that they are rotated in synchronism with the main shaft of the warp knitting machine so that they can effect positioning of the associated guide bars while the needles are in the lower positions.

Also, stitches usually of one course ae formed while the main shaft makes one complete rotation. Generally, stitches are formed by the needles while the main shaft rotates through the initial one-sixth of 360° or 600° and the final one-sixth or 60° thereof, and positioning of the guides are effected while the main shaft rotates through the intermediate two-thirds of 360° or 240°. The series of pulses $S_4$ supplied through the control means 90 to the pulse distributor 91 are transmitted to and actuate the pulse distributor while the main shaft rotates through the intermediate 240° and positioning of the guides is effected. Thus, if the maximum number of pulses required for giving instructions on one course of stitches of the desired pattern is 168 which moves the guids a distance corresponding to the fourteen pitches of needles and if the guide bars are moved for a distance corresponding to one pitch of the needles upon receipt of the pattern instructions when the number of pulses supplied from the encoder 104 to the pulse distributor 91 is also 168, then the distributor 91 equally divides 12 pulses among the 168 pulses of the instruction signal $S_4$ from the conrol means 90, so that one pattern signal pulse $S_2$ is supplied to each drive mechanism 92 each time 14 signal pulses are produced by the control means 90.

Figure 14:
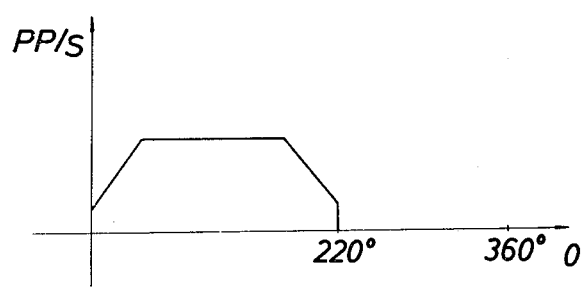
FIG. 14 shows one example of changes occurring in a unit time in the number of pulses used for driving each stepping motor according to the invention.

The intervals of the adjacent pulses of the signal $S_4$ from the control means 90 are gradually varied from one another as shown in FIG. 14. Thus, the stepping motors $PM_1$, $PM_2$-- $PMn$ rotate slowly immediately before forming of stitches is initiated and after completion of forming of stitches or when the guide bars begin to move and when positioning thereof is effected during one complete revolution of the main shaft, so that the movements of the stepping motors can be synchronized with the movements of the needles.

Figure 16:
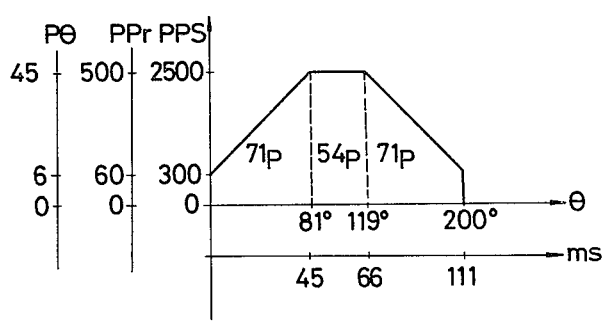
FIG. 16 shows another example of changes occurring in a unit time in the number of pulses as shown in FIG. 14.

FIG. 16 shows another pattern of the frequency (PPS) of output pulses of the encoder 104 or changes in the number of pulses in a given time intended to complete the movements of the guide bars during an angle range 200° in one complete revolution of the main shaft. According to this pattern, the rate of production of pulses is increased from 300 PPS to 2,500 PPS while the main shaft rotates through an angle range between 0° and 81°, the rate is maintained at 2,500 PPS while the main shaft rotates through an angle range between 81° and 119° so as to move the guide bars quickly during this time interval, and the rate is reduced from 2,500 PPS to 300 PPS while the main shaft rotates through an angle range between 119° and 200°, thereby terminating the movements of the guide bars. Assuming that the total number of pulses produced is 196, for example, then 71 pulses are produced while the main shaft rotates through the angle range between 0° and 81°, 54 pulses are produced while the main shaft rotates through the angle range between 81° and 119° and 71 pulses are generated while the main shaft rotates through the angle range between 119° and 200°.

The angle $P_\theta$ through which the main shaft rotates during the time the next following pulse is produced after the preceding pulse is produced can be obtained by the following formula. Assuming that the number of pulses produced in a unit time is A PPS when the main shaft rotates at R rpm $$P_\theta = \frac{360 \times \frac{1}{60}}{A}$$

If the time interval elapsing before the next following pulse is produced after the preceding pulse is produced is reduced linearly, then A can be expressed by the linear equation $A = an + b$. Hence, $$P_\theta = \frac{60R}{an+b}.$$

Figure 17:
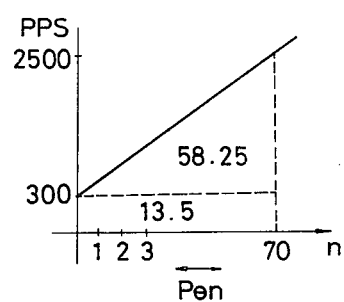
FIG. 17 is a view in explanation of the manner in which the number of pulses increases at initial stages of a unit time in which the number of pulses increases.

When the pattern of changes in the number of pulses produced in a given time is as shown in FIG. 17, A=300 if n=0 and A=2500 if n=70. Thus, a=220/7 and b=300. Hence, $$A = \frac{220}{7}n + 300.$$

Assuming that the number of revolutions of the main shaft is such that R rpm is 300, P$\theta$n can be obtained by the following formula:

$$P_\theta n = \frac{1800}{\frac{220}{7}n + 330} \qquad n = 0 \sim 70.$$

In the pattern shown in FIG. 16, $P_\theta$ is 6° when the rate of production of pulses is 300 PPS and about 45° when the rate of generation of pulses is 2500 PPS.

Thus, the stepping motors can be operated in synchronism with the main shaft so that the movements of the guide bars can be made to occur in timed relationship with respect to the movements of the needles.

Besides being rotated continuously, the main shaft 102 is subjected to an inching operation when inspection and adjustments are affected. It becomes necessary to move the main shaft course by course when adjustments are made in the position of the guides according to the desired pattern. When this is the case, an inching signal 105 or one course forming signal 106 is supplied directly to the main shaft rotation speed control means 103 without passing through the control means 90. Upon receipt of such signal, the main shaft rotation speed control means 103 gives instructions to the main shaft rotating motor M to rotate the main shaft slightly for an instant or rotate the main shaft through an angle corresponding to movements of guides for forming stitches of one course or generally 360°.

When the one course forming signal 106 is supplied to the main shaft rotation speed control means 103, the main shaft 102 should accurately rotate through an angle or 360°, for example, in order to cause the needles to form one course of stitches. In order to obviate the possibility of the main shaft rotating more than is necessary by inertia, the main shaft rotating motor M is provided with an electromagnetic brake 107 (See FIG. 12). The one course forming signal 106 is supplied to the electromagnetic brake 107, too. When the rotation angle detector 104 detects that the main shaft 102 has rotated through an angle necessary for forming stitches of one course, the detector 104 supplies a signal to the control means 90 which accordingly shuts off the main shaft rotation speed control means 103 and at the same time actuates the electromagnetic brake 107, thereby instantaneously stopping the rotation of the main shaft rotating motor.

If there is an error in the number of pulses or misoperation of parts occurs while the warp knitting machine is continuously operating under the control of the aforementioned control system to produce a knitting according to the desired pattern, the stitches formed in knitting produced will differ from the desired pattern or the needles will be damaged by striking against the guides. A safety mechanism may be provided in order to avoid such mishaps.

Figure 4:
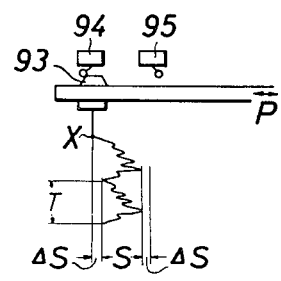
FIG. 4 is a fragmentary enlarged view of FIG. 3.

As shown in FIG. 3 and FIG. 4, each guide bar 1 is provided with a dog 93. On the other hand, two limit switches 94 and 95 are mounted on the machine frame for each dog 93. The limit switches 94 and 95, which are spaced apart from each other axially of the associated guide bar 1 for any distance as desired, may be moved to have their relative positions adjusted each time a pattern for the knittings to be produced is selected. If the maximum distance covered by the movement of each guide which may vary depending on the pattern selected for the knittings to be produced is called S as shown in FIG. 4, then the positions of the limit switches 94 and 95 are set such that one of them is actuated by the corresponding dog when the associated guide moves for a distance $\Delta S$ in excess of the maximum distance S in either direction.

Generally, the distance $\Delta S$ is set such that it is equal to the distance corresponding to one pitch of the guides so as to prevent the occurrence of disorder in the stitches formed or it is equal to the amount of a movement of a guide which brings the guide into collision with a needle. More specifically, if the width of each needle is called $t1$, if the width of each guide is called $t2$, and if the distance between the adjacent needles is called P, then the value for the distance $\Delta S$ is set at $\frac{1}{2}(P - t_1 - t_2)$. If each guide deviates from the predetermined maximum distance covered by its movement owing to an error in the number of pulses produced or some other cause and either one of the limit switches 94 and 95 is actuated, a warning signal is produced and the loom is shut off.

Figure 5:
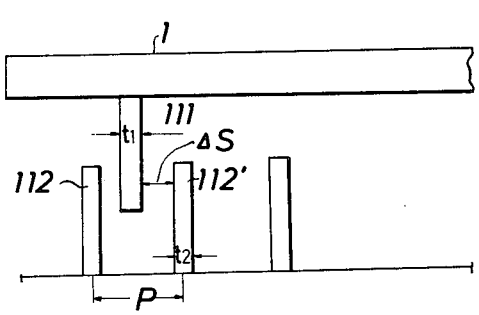
FIG. 5 is a fragmentary enlarged view of FIG. 4.

Each guide 111 shown in FIG. 5 will deviate from its correct position when there is an error in the movement of the associated push rod 3 due to thermal expansion or other cause, when the associated step motor is under the influence of any disturbance, or when the associated stepping motor goes wrong and its angle of rotation deviates from the correct value. If the amount of deviation of the guide 111 is smaller than the distance $\Delta s$ between the guide 111 and a latch needle 112 or 112' when the guide 111 is disposed midway between the adjacent latch needles 112 and 112', there will be no trouble because the guide 111 remains in a position between the latch needles 112 and 112'. However, if the amount of deviation of the guide 111 is greater than the distance $\Delta s$, the guide 111 will either overlap the latch needle 112 or 112' or move into the space between the adjacent latch needles, thereby shifting the position in which the stitch is formed. Let us assume that the width of the guide 111 is $t_1$, the width of the latch needles 112 and 112' is $t_2$, the distance corresponding to the pitch of the needles 112 and 112' is P, and the value of $$\Delta s \text{ is} \geq \frac{P-t_1-t_2}{2}.$$

Then, the guide will reach a point X at which it has moved for a distance ΔS in excess of the maximum distance S after the lapse of one cycle of operation T following the occurrence of any of the aforementioned abnormal conditions. At this time, the dog 93, for example, will have reached the position shown in FIG. 4 in which it actuates the limit switch 94. Thus, even if an abnormal condition occurs, the warp knitting machine will be shut off before one cycle of stitching operation is completed or the safety device is actuated to give an alarm.

A strain may be set up in the needle guides or guide bars when changes occur in the room temperature. This will cause changes in the value of one pitch of the needles. When this is the case, instructions given to the guide bars will supply no correct information if pulse signals are produced based on the theoretical value of one pitch, with a result that each guide bar will move a distance which does not suit the condition.

In order to correct this error, temperature-strain coefficients are calculated beforehand according to the materials used for the guide bars and needle guides, and correction signals are supplied to the pulse distributor 91 by using the data. More specifically, measured temperature values are converted by an analog/digital converter 97 into digital data which are supplied to a temperature-strain coefficient calculating unit 98 which produces a correction signal to a pitch value register 99, where the number of pulses set beforehand according to a predetermined number of pitches are varied to suit the prevailing room temperature. Then, the register 99 gives instructions to the pulse distributor 91 on the corrected value of one pitch corresponding to the prevailing room temperature, thereby compensating for changes in the value of one pitch of the needles.

In the pulse distributor 91, the number of pulses distributed to each stepping motor device is increased or decreased so as to move the associated guide bar to a correct position. In the initial stages of operation of the warp knitting machine, the value of one pitch of the needles set beforehand is stored in the pitch value register 99 and instructions are given to the pulse distributor 91 according to this value.

Stitches are formed on the thread according to the desired pattern as the rotation of the stepping motors causes the associated guide bars to move in linear reciprocatory movement. As aforementioned, the rotary movement of each stepping motor is transmitted to the associated guide bar through a mechanical transmission mechanism. Each guide bar is moved in linear reciprocatory movement by the rotation of the associated stepping motor. At this time, a backlash may occur in each transmission mechanism. Thus, this gives rise to a possibility that there is a time lag in the movement of the guide bar when instructions are given by the stepping motor to reverse its direction of movement. In order to compensate for the backlash, the amounts of backlash of the transmission mechanisms are measured beforehand before the warp knitting machine is operated continuously. For example, measurements of backlash are carried out with each guide bar in such a manner that the number of pulses is determined which represents the deviation of the guide bar from its original position when it reverses its direction of movement and moves for a distance corresponding to minus one pitch after moving for a distance corresponding to plus one pitch.

A backlash compensating value for each amount of movement of each guide bar calculated from the results of aforementioned measurements and stored beforehand in a backlash compensation means 100 provided for each guide bar. After each guide bar has reversed its direction of movement upon receipt of a signal from the memory 89, the reversal of the direction of movement is detected by a guide bar movement direction reversing detector 101 which produces and supplies a signal to the associated backlash compensation means 100. That is, the guide bar movement direction reversing detector 101 finds out that the signal for the next following course is converted from a plus signal into a minus signal or from a minus signal into a plus signal and triggers the backlash compensation means 100. Each time the backlash compensation means 100 is triggered, it produces a command signal to the pulse distributor 91 requiring to add to the number of pulses usually supplied to the stepping motor to move the guide bar the number of pulses which corresponds to the backlash compensating value which is stored in the backlash compensation means 100 for the respective point.

Upon receipt of the backlash compensating signal from the backlash compensation means 100, the pulse distributor 91 increases the number of pulses of the series of pulses distributed at that time. Thus, when each guide bar reverses its direction of movement after forming one course of stitches and before forming the next following course of stitches, the ssociated stepping motor receives through the pulse distributor 91 a supply of a series of pulses which is greater in number than the predetermined number of pulses by the number of pulses added thereto based on the backlash compensating signal. The stepping motor is driven by the backlash compensating pulses before it is driven by the predetermined number of pulses, so that the stepping motor can be driven accurately to form stitches according to the desired pattern.

Compensation for the backlash is effected for each guide bar or for each stepping motor. In order to simplify the construction of the backlash compensating device, backlash compensation values may be set for one guide bar only and such values may be applied to other guide bars. This simplifies the device but the degree of precision with which backlash compensation is effected is reduced.

The amount of backlash may be measured by determining the position of each guide bar by using a guide bar position detector means of the magnetic read-out type, e.g. the aforementioned Magnescale made by Sony Company, in an effort to determine the amount of displacement from a predetermined position. To be more precise, the amount of backlash may be measured by using a dial gauge or other measuring instrument.

Figure 18:
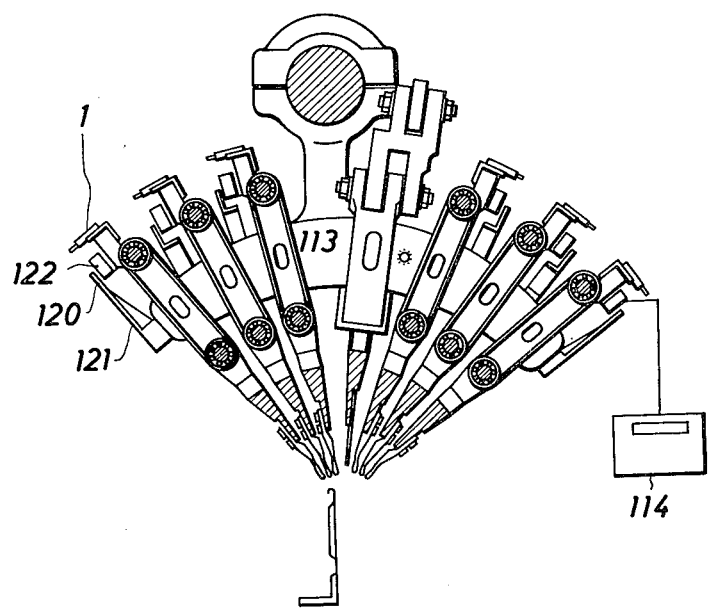
FIG. 18 shows the relation in arrangement between the guide bars and a magnetscale.

In FIG. 18, magnet scales 120 of the guide bar position detector means of the magnetic read-out type are each supported by a carrier 121 which is affixed to a guide bar supporter 113. Read-out heads 122 are each affixed to the associated guide bar 1. Alternatively, the magnet scale 120 consists of a scale magnetically graduated in 200 microns. The read-out head 122 is disposed in the vicinity of the associated magnet scale 120 and the position of the read-out head 122 relative to the scale 120 can be detected with the degree of precision of 100 to 2 microns from the value of an electric output signal produced thereby.

A signal indicating the position of each guide bar 1 relative to the guide bar supporter 113 or an associated latch needle as detected by the associated read-out head 122 is supplied to an indication device 114 including a counter to indicate the position of each guide bar. Preferably, the position indication device is constructed such that it not only indicates the amount of deflection of each guide bar from its regular position but also has a code mark attached thereto for indicating the direction of deflection. The amount of deflection of each guide bar may be returned by feedback to a control circuit for the drive mechanisms of the control apparatus so as to thereby correct the positions of the guide bars 1 during the operation of the warp knitting machine.

When it is desired to operate the warp knitting machine automatically, the position of each guide bar is detected by the aforementioned guide bar position detector means and reading of its position is obtained from position indication means. When any of the guide bars is displaced from its regular position, the position of the particular guide bar is corrected by reading the value thereof indicated by the position indication means, or the position of the associated latch needle is corrected. It is after the relative positions of the guide and the latch needle are corrected or ascertained in this way that the operation of the warp knitting machine is initiated. If necessary, the size of one pitch can be corrected and the blacklash compensating value can be varied automatically at all times by the feedback system while the warp knitting machine is in operation. However, this is conductive to increased operation cost.

As aforementioned, the present invention permits a warp knitting machine to operate automatically and continuously to form a course of stitches according to the desired pattern by instructions from the memory 87. Alternatively, in order to measure the amount of backlash of each guide bar before initiation of operation, it is possible to move only the guide bars irrespective of the rotation of the main shaft 102. To this end, the control means 90 may be provided with a drive system for automatically driving all the stepping motors or any one of them as desired.

For driving the stepping motors, a manually operated pulse oscillator 108 may be employed which produces pulses when a handle is operated by hand. The pulses produced by such manually operated pulse oscillator 108 are supplied to the drive mechanisms 92 so as to drive the stepping motors $PM_1$, $PM_2$ – $PMn$ according to the number of pulses produced.

From the foregoing description, it will be appreciated that the control apparatus according to the present invention permits the main shaft 102 to rotate synchronously with the stepping motors. Instructions given to the control means 90 initiate the rotation of the main shaft drive motor M to thereby drive the main shaft 102. At the same time, the memory 89 is actuated to give instructions to the stepping motors in the form of pulse signals which may vary in number depending on the desired pattern according to which knittings are to be produced. Thus, each guide bar is individually driven by the associated stepping motor according to the number of pulses and whether the pulses are positive or negative, whereby stitches can be automatically formed according to the desired pattern. When the power source of the control apparatus involving the electronic computer is switched off during the operation of it, the information stored in an arithmetic unit of the control apparatus is cleared, so that the pattern signal to be fed to the servo drive mechanisms are discontinued and no pulses can be fed to the servo drive mechanisms. This produces an inferior pattern when the knitting machine is started again under the condition as it is. For avoiding this disadvantage, it is necessary that the power source is to be switched off after confirmation of a completion of the pulse train providing the one course of the pattern.

In order to operate the control apparatus satisfactory on the occasion of the interruption by switching off the power source, in this invention it is considered that the main switch can be switched off automatically after completion of one course feeding of the pattern signal.

In this invention the control apparatus may be operated as follows.

By pushing of main switch OFF button of the warp knitting machine or the control apparatus the signal for reducing the speed of the main shaft is supplied from the control means 90 to the main shaft speed control means 103. By detecting of the main shaft speed reduced to a predetermined low speed by means of the main shaft speed detector the control means 90 is activated and it gives a signal for interrupting a proceeding of the program to the memory 89. After feeding of the signal for providing one course pattern to the pulse distributor 91 the memory 89 interrupts the proceeding of the program and gives a signal, for stopping the main shaft, to the main shaft speed control means 103. The main shaft is stopped and clamped in a range before knitting by needles. In the control means 90 the number of the last course supplied from the memory to the pulse distributor is typed out. The control means supplies a signal for switching off the power source to the knitting machine and to control apparatus simultaneously or with a time lag.

It is possible that the main shaft can be braked in one step, not two step as described hereinbefore, but in this case the main shaft may be stopped in irregular position by reason of the mechanical shock and inertia.

In this invention the main shaft is stopped with steps, so that a cut of thread may be prevented and the long life of the machine can be obtained.

What I claim is:

1. A control apparatus for controlling the movement of the guide bars of a warp knitting machine, having a main shaft, in accordance with a desired pattern and in synchronism with the rotation of the main shaft, said control apparatus comprising, in combination, a memory operable to store information corresponding to successive courses of a pattern to be knit; a pulse distributor connected to said memory; means, including a shaft rotation angle detector connected to said main shaft, operable, responsive to rotation of said main shaft in a predetermined angular range, to produce a plurality of pulse trains and to supply the same to said pulse distributor; control means connected to said memory and operable, responsive to input of an instruction, to control said memory to supply successive pattern course signals to said pulse distributor; and a number of servo mechanisms, equal to the number of guide bars, connected to said pulse distributor and each including a rotatable servo motor and means for converting the rotary output of the associated servo motor into a linear movement of a respective guide bar; said pulse distributor, responsive to such pattern course signals supplied thereto from said memory, supplying respective pulse trains to said servo mechanism to move the associated guide bars respective distances corresponding to the respective pattern course to be knit; said servo drive mechanisms each comprising a stepping motor and means for converting a rotary movement into a linear movement and which converts the angle of rotation of an output shaft of the respective stepping motor into a corresponding magnitude linear movement of the associated guide bar; said means for converting the rotary movement into a linear movement comprising a threaded shaft, a nut threadedly mounted on said threaded shaft and guided by a fixed frame for linear sliding motion, and means transmitting the linear reciprocatory movement of said nut to a push rod connected to the associated guide bar.

2. A control apparatus as claimed in claim 1, in which said means for transmitting the linear reciprocatory movement of said nut to a push rod connected to the associated guide bar comprises a ball spline shaft supported by said fixed frame for coaxial movement with said push rod.

3. A control apparatus as claimed in claim 1 in which said servo drive mechanisms each comprise a hydraulic actuator driven through electro-hydraulic control valves with said pulses and a means for converting a rotary movement into a linear movement.

4. A control apparatus as claimed in claim 1 in which said servo drive mechanisms each comprise a DC motor and a means for converting a rotary movement into a linear movement.

5. A control apparatus as claimed in claim 3 further characterized in that said hydraulic actuator is a hydraulic motor with rotatable output shaft, and said means for converting a rotary movement into a linear movement is adapted to convert the angle of a rotation of an output shaft of a said hydraulic motor into the amount of a linear movement of the associated guide bar and comprises a threaded shaft connected to the output shaft of the hydraulic motor, a nut threadably mounted on said threaded shaft and guided by a fixed frame for linear sliding motion, and a ball spline shaft adapted to transmit a linear reciprocatory movement of said nut to a push rod connected to the associated guide bar, said ball spline shaft being supported by said fixed frame for coaxial movement with said push rod.

6. A control apparatus as claimed in claim 4 further characterized in that said means for converting a rotary movement into a linear movement comprises a threaded shaft connected to an output shaft of said DC motor, a nut threadably mounted on said threaded shaft and guided by a fixed frame for linear sliding motion, and a ball spline shaft adapted to transmit a linear reciprocatory movement of said nut to a push rod connected to the associated guide bar, said ball spline shaft being supported by said fixed frame for coaxial movement with said push rod.

7. A control apparatus as claimed in claim 1 in which said servo drive mechanisms each comprise a servo motor, a threaded shaft connected to an output shaft of said servo motor, a nut threadably mounted on said threaded shaft and guided by a servo drive mechanism supporting frame for linear sliding motion, and a flexible tensile force transmitting member connected at one end to said nut and at the other end to a member for moving the associated guide bar.

8. A control apparatus as claimed in claim 7 further comprising a correction device comprising a ratchet wheel connected to said tensile force transmitting members and having teeth of the same pitch as the pitch of needles of the warp knitting machine, a pawl adapted to engage one of said teeth of said ratchet wheel, an eccentric shaft pivotally supporting said pawl and supported by a machine frame for rotation about an eccentric axis, means for causing said pawl pivotally to move about said eccentric shaft so as to bring the pawl into and out of engagement with one of said teeth of said ratchet wheel, and correction means causing said eccentric shaft to ratate about said eccentric axis to move the pawl so as to shift the same whereby the position in which the pawl engages a tooth of the ratchet wheel can be moved a distance corresponding to one pitch of the teeth, said correction means being effective to render said tensile force transmitting members impervious to an error in the number of pulses and other influences and disturbances to ensure that each tensile force transmitting member moves a distance corresponding to an integral muliiple of a predetermined length.

9. A control apparatus as claimed in claim 1 in which said servo drive mechanisms each comprises a servo motor, a threaded shaft connected to an output shaft of said servo motor, a nut threadably mounted on said threaded shaft and guided by a fixed frame for linear sliding motion, and a pin drum arrangement for transmitting the amount of a linear movement of said nut to the associated guide bar, said pin drum arrangement comprising a drum supported for rotation, a plurality of pins arranged radially and equidistantly in said drum for movement radially of the drum toward and away from the center of the drum, a plurality of springs each adapted to bias the associated pin radially outwardly of the drum, a plurality of ratchet wheels, and a plurality of pawls, one of said plurality of ratchet wheels and a pair of said plurality of pawls cooperating with one another to keep the associated pin in a position which is set by said nut.

10. A control apparatus as claimed in claim 9 in which said pin drum arrangement comprises a drum supported for rotation by a drive mechanism mounting frame, a plurality of pins arranged radially and equidistantly in said drum for movement radially of the drum toward and away from the center of the drum, a plurality of pinions rotatably supported on the drum and each adapted to mesh with a rack formed in one of said plurality of pins, a plurality of ratchet wheels, a plurality of pawls, one of said plurality of ratchet wheels and a pair of said plurality of pawls cooperating with one another to lock the associated pinion in a desired position, a cam adapted to control the movement of each said pair of pawls between a position in which they engage the associated ratchet wheel and a position in which they are out of engagement therewith, a plurality of bridges each adapted to interconnect the adjacent two pins.

11. A control apparatus as claimed in claim 1 in which control of the guide bars is effected during the time when the main shaft of the warp knitting machine rotates through a portion of a predetermined angle and that stitches are formed by needles during the time when the main shaft rotates through the rest of the predetermined angle of rotation required for completing the formation of one course of stitches, said a pulse distributor being adapted to select pulses from the pulses received from said rotation detector in any rate determined by the pattern instruction signal and supply them to each servo mechanism as pattern instruction pulses according to the pattern instruction signal.

12. A control apparatus as claimed in claim 11 in which angle detector comprises at least one encoder of the rotary type formed with slits and adapted to produce a predetermined number of pulses during the time when control of the guide bars is effected, the spacing between the adjacent slits being gradually reduced in the initial stages of an operation for effecting control of the guide bars and gradually spaced apart from one another in the intermediate stages.

13. A control apparatus according to claim 1 further comprising a temperature measuring means, a converter for converting measured temperature values into digital data, a temperature-strain coefficient calculating means adapted to calculate from each of said digital data a strain co-efficient which is a function of the temperature, and a pitch value register for storing therein the value of one pitch of needles set beforehand, said temperature-strain coefficient calculating means supplying a correction signal to said register where the number of pulses corresponding to the correction signal is added to or deducted from the number of pulses corresponding to the value of one pitch stored in the register, and said register supplying pulses to the pulse distributor after correction is made in their number so as to thereby vary the number of pulses required for driving the associated stepping motor to move the associated guide bar for a distance corresponding to the modified pitch of the needles.

14. A control apparatus as claimed in claim 1 further comprising a backlash compensation means storing therein a backlash compensating value of each said servo drive mechanism for the associated guide bar, and a guide bar movement direction reversing detector adapted to detect the reversing of the direction of mevement of each said guide bar and giving instructions to said backlash compensating means, said pulse distributor means receiving a pattern signal for each course produced as a result of analysis of the desired pattern and a signal from the backlash compensating means and transmitting pattern instruction pulses added with pulses corresponding in number to the backlash compensating value to each servo drive mechanism when instructions are given by said guide bar movement direction reversing means to said backlash compensating means.

15. A control apparatus as claimed in claim 1, further including a main motor operable to rotate said main shaft, a main shaft rotation speed control connected to said control means and to said main motor, and an electromagnetic brake, said main shaft rotation speed control and said electromagnetic brake being controlled by said control means, said angle detector being adapted to detect the completion of rotation of said main shaft through an angle corresponding to an operation of needles required for completing one course of stitches and to supply a signal to said control means, said control means supplying, to said main shaft rotation speed control and to said electromagnetic brake a signal that an operation for forming one course of stitches has been completed, whereby said electromagnetic brake interrupts the rotation of said main motor after said main motor has rotated said main shaft through said angle corresponding to the operation of the needles required for completion of one course of stitches.

16. A control apparatus as claimed in claim 1, further comprising dogs and limit switches, each dog being operatively associated with a respective pair of spaced limit switches, and each dog and its associated pair of limit switches being movable relative to each other responsive to movement of a respective guide bar, each dog and the associated pair of limit switches being so disposed that a respective limit switch is operable by the associated dog at the limit of movement of the associated guide bar, each limit switch being operable to interrupt the operation of said main shaft and the associated servo driving mechanism when the respective guide bar moves further than a predetermined maximum distance from the center between adjacent needles for a displacement by an amount expressed by the following formula:

$$s = \frac{P - t_1 - t_2}{2}$$

where
 $P$ = the pitch of the needles;
 $t_1$ = the thickness of each guide; and
 $t_2$ = the thickness of each needle.

17. A control apparatus as claimed in claim 1, including a main shaft speed control connected to said control means and operatively associated with said main shaft, said control means supplying a signal, for reducing the speed of said main shaft, through said main shaft speed control responsive to operation of a main switch OFF button of said control apparatus; a main shaft speed detector operatively associated with said control means and said main shaft, said control means supplying a signal, for interrupting progress of the program, to the memory, by detecting reduction of the speed of the main shaft to a predetermined low speed by the main shaft speed detector, said control means supplying a signal, for braking of the main shaft, to said main shaft speed control responsive to receipt of a signal of completion of the supply of one course signal from said memory, and said control means supplying the number of the last course supplied from said memory to said pulse distributor, said control means supplying a signal to shut off the power source of the knitting machine and the control apparatus.

* * * * *